(12) United States Patent
Sugiyama et al.

(10) Patent No.: US 8,248,500 B2
(45) Date of Patent: Aug. 21, 2012

(54) SOLID STATE IMAGING DEVICE

(75) Inventors: Yukinobu Sugiyama, Hamamatsu (JP);
Seiichiro Mizuno, Hamamatsu (JP)

(73) Assignee: Hamamatsu Photonics K.K.,
Hamamatsu-shi, Shizuoka (JP)

( * ) Notice: Subject to any disclaimer, the term of this patent is extended or adjusted under 35 U.S.C. 154(b) by 869 days.

(21) Appl. No.: 12/162,386

(22) PCT Filed: Jan. 30, 2007

(86) PCT No.: PCT/JP2007/051485
§ 371 (c)(1),
(2), (4) Date: Oct. 1, 2008

(87) PCT Pub. No.: WO2007/086576
PCT Pub. Date: Aug. 2, 2007

(65) Prior Publication Data
US 2009/0073295 A1    Mar. 19, 2009

(30) Foreign Application Priority Data
Jan. 30, 2006  (JP) ................................ P2006-021228

(51) Int. Cl.
*H04N 3/14*    (2006.01)
*H04N 5/335*   (2011.01)

(52) U.S. Cl. ...................................... 348/302

(58) Field of Classification Search .................... 348/302
See application file for complete search history.

(56) References Cited

U.S. PATENT DOCUMENTS
5,887,049 A * 3/1999 Fossum ........................ 378/98.8
6,307,915 B1 * 10/2001 Frojdh ......................... 378/98.8
2002/0101527 A1    8/2002 Endo
2003/0146991 A1 * 8/2003 Barna et al. ................. 348/302

FOREIGN PATENT DOCUMENTS

| GB | 2 304 017    | 3/1997  |
|----|--------------|---------|
| JP | 5-130990     | 5/1993  |
| JP | 11-188033    | 7/1999  |
| JP | 2001-299734  | 10/2001 |
| JP | 2002-505002  | 2/2002  |
| JP | 2002-181942 A| 6/2002  |
| JP | 2004-130058  | 4/2004  |
| WO | WO 03/032839 | 4/2003  |

* cited by examiner

*Primary Examiner* — Scott J Sugarman
*Assistant Examiner* — Vipin Patel
(74) *Attorney, Agent, or Firm* — Drinker Biddle & Reath LLP

(57) ABSTRACT

A solid-state image pickup device 1 includes an imaging photodetecting section 10, a triggering photodetecting section 20, a row selecting section 30, a column selecting section 40, a voltage holding section 50, an output section 60, and a controlling section 70. The imaging photodetecting section 10 is for taking an image of incident light, and includes pixel sections $P_{1,1}$ to $P_{M,N}$ arrayed two dimensionally in M rows and N columns. The triggering photodetecting section 20 is for detecting an incidence of light, and includes a triggering photodiode that generates electric charge of an amount according to an incident light intensity. The output section 60 outputs pixel data of a value according to the amount of electric charge generated by a photodiode of any pixel section $P_{m,n}$ of the pixel sections $P_{1,1}$ to $P_{M,N}$ included in the imaging photodetecting section 10 and triggering data of a value according to the amount of electric charge generated by the triggering photodiode included in the triggering photodetecting section 20 to a common output signal line Lout.

2 Claims, 5 Drawing Sheets

SOLID STATE IMAGING DEVICE

TECHNICAL FIELD

The present invention relates to a solid-state image pickup device having a photodetecting section for which a plurality of photodiodes that each generate electric charge of an amount according to an incident light intensity are arranged two dimensionally, and particularly, to a solid-state image pickup device that can be suitably used for oral radiography.

BACKGROUND ART

A solid-state image pickup device intended to be used for oral radiography has been disclosed in Patent Document 1. For such application, the period of incidence of X-rays to be imaged is considerably short so that the solid-state image pickup device must capture the timing of incidence of X-rays to image the X-rays. Therefore, the solid-state image pickup device disclosed in Patent Document 1 also includes a triggering photodiode for detecting an incidence of X-rays separately from an imaging photodetecting section including a plurality of photodiodes arrayed two dimensionally in order to take an X-ray image. And, this solid-state image pickup device detects an incidence of X-rays by monitoring an electrical signal outputted from the triggering photodiode and then obtains an X-ray image based on an electrical signal outputted from the imaging photodetecting section.
Patent Document 1: Japanese Translation of International Application (Kohyo) No. 2002-505002

DISCLOSURE OF THE INVENTION

Problem to be Solved by the Invention

However, the solid-state image pickup device disclosed in the above Patent Document 1 has a large number of wirings for input and output signals and the like with an external apparatus and thus has a low reliability as one used in the oral cavity. The present invention has been made in order to solve the above problem, and an object thereof is to provide a solid-state image pickup device that can be improved in reliability and can also be suitably used in an oral cavity.

Means for Solving the Problem

A solid-state image pickup device according to the present invention includes: (1) an imaging photodetecting section including pixel sections $P_{1,1}$ to $P_{M,N}$ each having a photodiode that generates electric charge of an amount according to incident light intensity and arrayed two dimensionally in M rows and N columns; (2) a triggering photodetecting section including a triggering photodiode that generates electric charge of an amount according to incident light intensity; and (3) an output section that outputs pixel data of a value according to the amount of electric charge generated by the photodiode of any pixel section $P_{m,n}$ of the pixel sections $P_{1,1}$ to $P_{M,N}$ and triggering data of a value according to the amount of electric charge generated by the triggering photodiode to a common output signal line. Here, M and N are integers not less than 2, m is an integer not less than 1 and not more than M, and n is an integer not less than 1 and not more than N.

In the solid-state image pickup device according to the present invention, pixel data of a value according to the amount of electric charge generated by the photodiode of any pixel section $P_{m,n}$ of the pixel sections $P_{1,1}$ to $P_{M,N}$ included in the imaging photodetecting section and triggering data of a value according to the amount of electric charge generated by the triggering photodiode included in the triggering photodetecting section are outputted from the output section to the common output signal line. In an external apparatus that is used in connection with this solid-state image pickup device, based on the triggering data outputted from the output section of the solid-state image pickup device to the output signal line, whether light has been made incident into the solid-state image pickup device is recognized, and based on the pixel data outputted from the output section of the solid-state image pickup device to the output signal line, an image of light made incident into the solid-state image pickup device is obtained.

In the solid-state image pickup device, since the pixel data and the triggering data are outputted to the common output signal line by time sharing, the solid-state image pickup device suffices with a small number of wirings to input and output signals and the like with an external apparatus and thus has a high reliability as one used in the oral cavity. Also, the pixel data and the triggering data that are outputted from the output section to the common output signal line may be either analog data or digital data, and in the latter case, this is preferably serial data.

In the solid-state image pickup device according to the present invention, it is preferable that the output section outputs the triggering data between a period to output pixel data of a value according to the amount of electric charge generated by the photodiode of each of the N pixel sections $P_{m1,1}$ to $P_{m1,N}$ of any m1-th row in the imaging photodetecting section and a period to output pixel data of a value according to the amount of electric charge generated by the photodiode of each of the N pixel sections $P_{m2,1}$ to $P_{m2,N}$ of another m2-th row. Here, m1 and m2 are integers not less than 1 and not more than M. By thus outputting the triggering data between the periods to output pixel data of each of the N pixel sections $P_{m,1}$ to $P_{m,N}$ of each row, the timing of incidence of light into the solid-state image pickup device can be accurately recognized.

In the solid-state image pickup device according to the present invention, it is preferable that the output section outputs, before a period to output pixel data of a value according to the amount of electric charge generated by the photodiode of each of the N pixel sections $P_{m,1}$ to $P_{m,N}$ of any m-th row in the imaging photodetecting section, row identifying data indicating the m-th row to the output signal line. By thus outputting row identifying data indicating the m-th row before a period to output pixel data of each of the N pixel sections $P_{m,1}$ to $P_{m,N}$ of the m-th row, it becomes possible for an external apparatus, which is the destination of a signal, to clearly distinguish what row of pixel data is being transmitted, so that an image of light made incident into the solid-state image pickup device can be accurately obtained.

In the solid-state image pickup device according to the present invention, it is preferable that the triggering photodetecting section includes one triggering photodiode provided surrounding the imaging photodetecting section. Moreover, it is also preferable that the triggering photodetecting section includes a plurality of triggering photodiodes provided around the imaging photodetecting section and connected to each other. By thus forming the triggering photodetecting section, an incidence of light into the solid-state image pickup device can be detected at a high sensitivity.

Effects of the Invention

The solid-state image pickup device according to the present invention can be improved in reliability and can also be suitably used in an oral cavity.

DESCRIPTION OF SYMBOLS

1 Solid-state image pickup device
10 Imaging photodetecting section
20 Triggering photodetecting section
30 Row selecting section
40 Column selecting section
50 Voltage holding section
60 Output section
61 Difference operating circuit
62 Integration circuit
63 A/D converter circuit
70 Control section
$P_{1,1}$-$P_{M,N}$ Pixel section

BEST MODES FOR CARRYING OUT THE INVENTION

Hereinafter, a best mode for carting out the present invention will be described in detail with reference to the accompanying drawings. Here, in the description of the drawings, identical elements are designated with identical numerical symbols so as to avoid overlapping descriptions.

Figure 1:
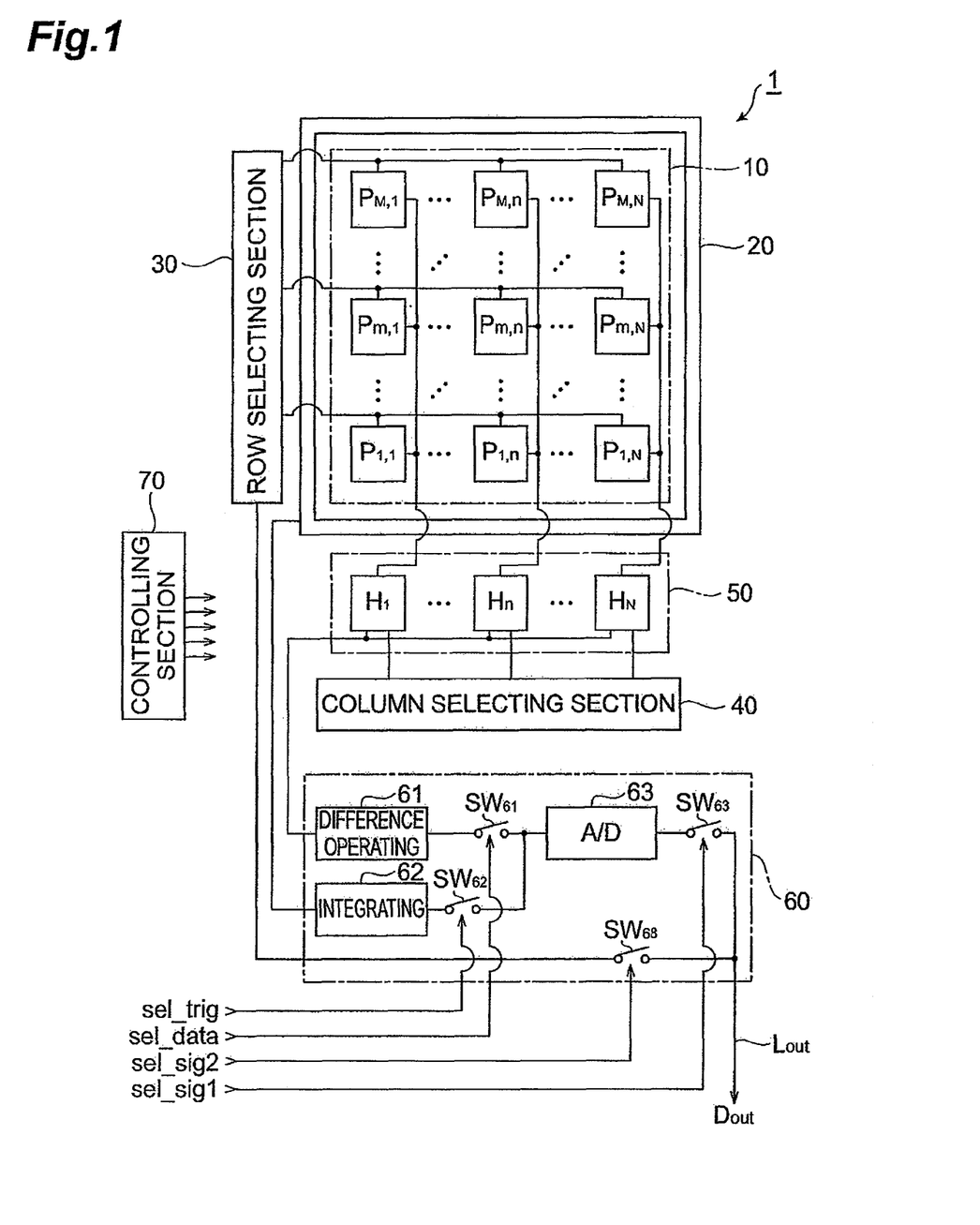
FIG. 1 is a configuration diagram of a solid-state image pickup device 1 according to the present embodiment.

FIG. 1 is a configuration diagram of a solid-state image pickup device 1 according to the present embodiment. The solid-state image pickup device 1 shown in this figure includes an imaging photodetecting section (imaging region) 10, a triggering photodetecting section 20, a row selecting section 30, a column selecting section 40, a voltage holding section 50, an output section 60, and a controlling section 70. Also, in this figure, wirings between elements are omitted or simplified.

The imaging photodetecting section 10 is a section for taking an image of incident light, and includes pixel sections $P_{1,1}$ to $P_{M,N}$ arrayed two dimensionally in M rows and N columns. A pixel section $P_{m,n}$ is located at the m-th row and the n-th column. The M×N pixel sections $P_{1,1}$ to $P_{M,N}$ have a common configuration and each include a photodiode that generates electric charge of an amount according to the incident light intensity. Here, M and N are integers not less than 2, m is an integer not less than 1 and not more than M, and n is an integer not less than 1 and not more than N.

Figure 5:
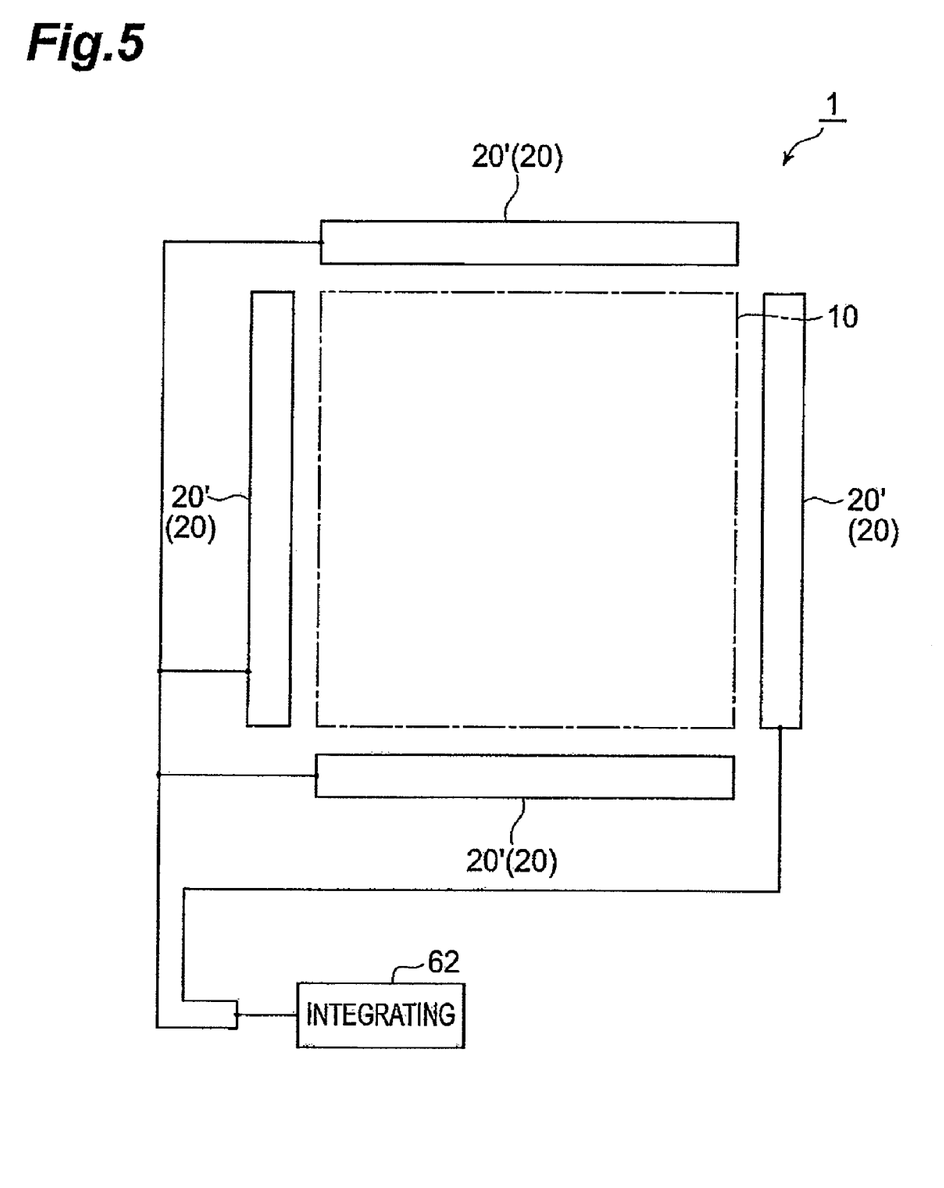
FIG. 5 is a view showing a modification of a triggering photodetecting section 20 of the solid-state image pickup device 1 according to the present embodiment.

The triggering photodetecting section 20 is a section for detecting an incidence of light, and includes a triggering photodiode (coincident with the triggering photodetecting section 20) that generates electric charge of an amount according to the incident light intensity. The number and arrangement of triggering photodiodes included in the triggering photodetecting section 20 can assume various modes, however, for detecting an incidence of light at a high sensitivity, it is preferable that the triggering photodiode is provided so as to surround the imaging photodetecting section 10, and moreover, it is preferable that the photodetecting section has a large area (area of a photosensitive section). It is preferable that the triggering photodetecting section 20 includes one triggering photodiode provided surrounding the imaging photodetecting section 10 as illustrated or, alternatively, as shown in FIG. 5, it is also preferable that the triggering photodetecting section 20 includes a plurality of triggering photodiodes 20' provided around the imaging photodetecting section 10 and connected parallel to each other. It suffices for the plurality of triggering photodiodes 20' that their respective cathodes are connected in common and anodes are both grounded.

The row selecting section 30 sequentially designates each row in the imaging photodetecting section 10 to output pixel data of a value according to the amount of electric charge generated by the photodiode of each of the N pixel sections $P_{m,1}$ to $P_{m,N}$ of the designated m-th row to the voltage holding section 50. The row selecting section 30 includes an unillustrated M-stage shift register circuit, and by an output bit of each stage of this shift register circuit, each row in the imaging photodetecting section 10 can be sequentially designated.

The voltage holding section 50 includes N holding circuits $H_1$ to $H_N$ having a common configuration. The holding circuit $H_n$ is connected with the M pixel sections $P_{1,n}$ to $P_{m,n}$ of the n-th column in the imaging photodetecting section 10, is inputted with the pixel data outputted from any pixel section $P_{m,n}$ of these, and holds and outputs the pixel data thus inputted. The holding circuit $H_n$ not only holds pixel data indicating a signal component superimposed with a noise component but can also hold pixel data indicating a noise component.

The column selecting circuit 40 sequentially designates the N holding circuits $H_1$ to $H_N$ included in the voltage holding section 50 to output pixel data held by the designated n-th holding circuit $H_n$ to the output section 60. The column selecting section 40 includes an unillustrated N-stage shift register circuit, and by an output bit of each stage of this shift register circuit, the N holding circuits $H_1$ to $H_N$ can be sequentially designated.

The output section 60 outputs pixel data of a value according to the amount of electric charge generated by the photodiode of any pixel section $P_{m,n}$ of the pixel sections $P_{1,1}$ to $P_{M,N}$ included in the imaging photodetecting section 10 and triggering data of a value according to the amount of electric charge generated by the triggering photodiode included in the triggering photodetecting section 20 to a common output signal line Lout. Also, the output section 60 is inputted with the pixel data from the voltage holding section 50 and is inputted with the triggering data from the triggering photodetecting section 20.

It is also preferable that the output section 60 outputs triggering data between a period to output pixel data of a value according to the amount of electric charge generated by the photodiode of each of the N pixel sections $P_{m1,1}$ to $P_{m1,N}$ of any m1-th row in the imaging photodetecting section 10 and a period to output pixel data of a value according to the amount of electric charge generated by the photodiode of each of the N pixel sections $P_{m2,1}$ to $P_{m2,N}$ of another m2-th row. Here, m1 and m2 are integers not less than 1 and not more than M.

It is also preferable that the output section 60 outputs, before a period to output pixel data of a value according to the amount of electric charge generated by the photodiode of each of the N pixel sections $P_{m,1}$ to $P_{m,N}$ of any m-th row in the imaging photodetecting section 10, row identifying data indicating the math row to the output signal line Lout. Also, the output section 60 is inputted with the row identifying data from the row selecting portion 30.

The output section 60 includes a difference operating circuit 61, an integrating circuit 62, an A/D converter circuit 63, and switches $SW_{61}$ to $SW_{63}$ and $SW_{68}$. The switch $SW_{61}$ is controlled by a sel_data signal to perform an opening/closing operation. The switch $SW_{62}$ is controlled by a sel_trig signal to perform an opening/closing operation. The switch $SW_{63}$ is controlled by a sel_sig1 signal to perform an opening/closing operation. Moreover, the switch$_{68}$ is controlled by a sel_sig2 signal to perform an opening/closing operation.

The difference operating circuit 61 is inputted with the pixel data indicating a signal component superimposed with a noise component from the holding circuit $H_n$ and is also inputted with the pixel data indicating a noise component from the holding circuit $H_n$, and outputs pixel data of a value according to a difference therebetween. The pixel data outputted from the difference operating circuit 61 indicates a signal component from which a noise component has been removed. The integrating circuit 62 is inputted with and accumulates an electric charge outputted from the triggering photodetecting section 20 and outputs a voltage value according to the amount of accumulated electric charge as triggering data. The switches $SW_{61}$ and $SW_{62}$ select either of the pixel data outputted from the difference operating circuit 61 and the triggering data outputted from the integrating circuit 62 and input the same to the A/D converter circuit 63.

The A/D converter circuit 63 is inputted with the pixel data outputted from the difference operating circuit 61 and arrived through the switch $SW_{61}$, A/D-converts the inputted pixel data (analog data), and outputs the same as digital data. Moreover, the A/D converter circuit 63 is inputted with the triggering data outputted from the integrating circuit 62 and arrived through the switch $SW_{62}$, A/D-converts the inputted triggering data (analog data), and outputs the same as digital data. The switches $SW_{63}$ and $SW_{68}$ select either of the pixel data or triggering data outputted from the A/D converter circuit 63 and the row identifying data outputted from the row selecting section 30 and makes the selected output data Dout be outputted to the output signal line Lout. Also, from the perspective of a reduction in the number of wirings, it is preferable that the output data Dout to be outputted to the output signal line Lout is serial data.

The controlling section 70 controls operation of the solid-state image pickup device 1 as a whole. For example, the controlling section 70 controls a row selecting operation in the row selecting section 30, a column selecting operation in the column selecting section 40, a data holding operation in the voltage holding section 50, opening/closing operations of the switches $SW_{61}$ to $SW_{63}$ and $SW_{68}$ included in the output section 60, a charge accumulating operation in the integrating circuit 62, and an A/D converting operation in the A/D converter circuit 63.

Figure 2:
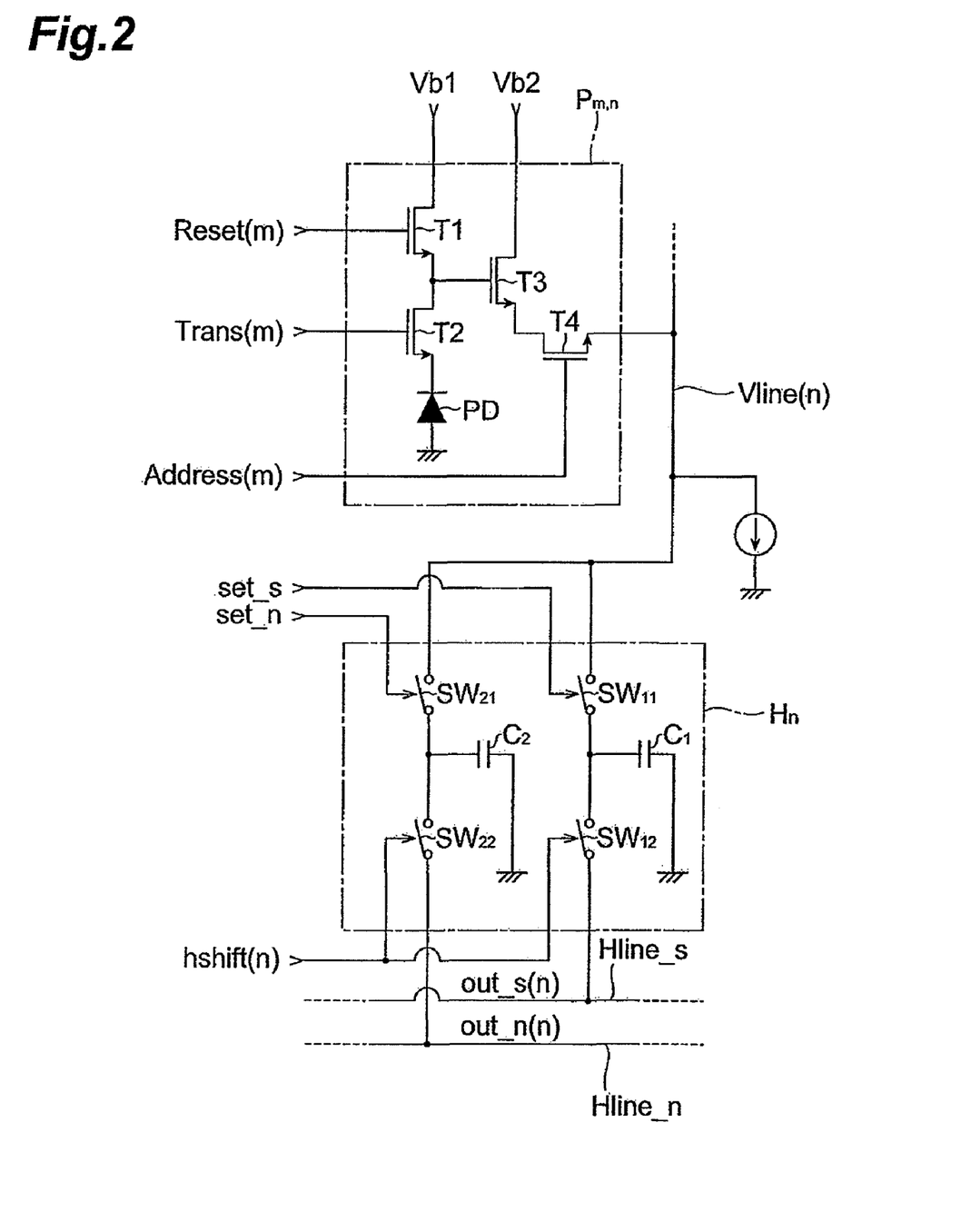
FIG. 2 is a diagram showing circuit configurations of a pixel section $P_{m,n}$ and a holding circuit $H_n$ included in the solid-state image pickup device 1 according to the present embodiment, respectively.

FIG. 2 is a diagram showing circuit configurations of the pixel section $P_{m,n}$ and the holding circuit $H_n$ included in the solid-state image pickup device 1 according to the present embodiment, respectively. In this figure, the pixel section $P_{m,n}$ is shown as representative of the M×N pixel sections $P_{1,1}$ to $P_{M,N}$ and the holding circuit $H_n$ is shown as representative of the N holding circuits $H_1$ to $H_N$.

The pixel section $P_{m,n}$ is of an APS (Active Pixel Sensor) type, and includes a photodiode PD and four transistors T1 to T4. As shown in this figure, the transistor T1, the transistor T2, and the photodiode PD are connected in series in order, and a reference voltage Vb1 is inputted to a drain terminal of the transistor T1, and an anode terminal of the photodiode PD is grounded. The transistor T3 and the transistor T4 are connected in series, and a reference voltage Vb2 is inputted to a drain terminal of the transistor T3, and a source terminal of the transistor T4 is connected to a wiring Vline(n). A junction point between the transistor T1 and the transistor T2 is connected to a gate terminal of the transistor T3. Moreover, a constant current source is connected to the wiring Vline(n).

A Reset(m) signal supplied from the row selecting section 30 is inputted to a gate terminal of the transistor T1, a Trans (m) signal supplied from the row selecting section 30 is inputted to a gate terminal of the transistor T2, and an Address (m) signal supplied from the row selecting section 30 is inputted to a gate terminal of the transistor T4. The Reset(m) signal, the Trans(m) signal, and the Address(m) signal are inputted to the N pixel sections $P_{m,1}$ to $P_{m,N}$ of the m-th row in common.

At the time of resetting, when the Reset(m) signal and the Trans(m) signal are at a high level, a junction capacitance section of the photodiode PD is discharged. When the Reset (m) signal and the Trans(m) signal are brought to a low level after discharging and further the Address(m) is brought to a high level, a noise component is outputted from the pixel section $P_{m,n}$ to the wiring Vline(n).

At the time of imaging, when the Reset(m) signal is at a low level and the Trans(m) signal and the Address(m) signal are at a high level, a voltage value according to the amount of electric charge accumulated in the junction capacitance section of the photodiode PD is outputted to the wiring Vline(n) as a signal component.

The holding circuit $H_n$ includes two capacitors $C_1$ and $C_2$ and four switches $SW_{11}$, $SW_{12}$, $SW_{21}$, and $SW_{22}$. In this holding circuit $H_n$, the switch $SW_{11}$ and the switch $SW_{12}$ are provided between the wiring Vline(n) and a wiring Hline_s while being connected in series, and one end of the capacitor $C_1$ is connected to a junction point between the switch $SW_{11}$ and the switch $SW_{12}$, and the other end of the capacitor $C_1$ is grounded. Moreover, the switch $SW_{21}$ and the switch $SW_{22}$ provided between the wiring Vline(n) and a wiring Hline_n while being connected in series, and one end of the capacitor $C_2$ is connected to a junction point between the switch $SW_{21}$ and the switch $SW_{22}$, and the other end of the capacitor $C_2$ is grounded.

In this holding circuit $H_n$, the switch $SW_{11}$ is opened and closed according to the level of a set_s signal supplied from the controlling section 70. The switch $SW_{21}$ is opened and closed according to the level of a set_n signal supplied from the controlling section 70. The set_s signal and the set_n signal are inputted to the N holding circuits $H_1$ to $H_N$ in common. The switches $SW_{12}$ and $SW_{22}$ are opened and closed according to the level of an hshift(n) signal supplied from the controlling section 70.

In this holding circuit $H_n$, operation is as follows.

At the time of resetting, the noise component that is being outputted from the pixel section $P_{m,n}$ to the wiring Vline(n) when the set_n signal is switched from a high level to a low level and the switch $SW_{21}$ is opened is, from then onward, held by the capacitor $C_2$ as a voltage value out_n(n). At this time of resetting, the switch $SW_{11}$ on a pixel signal acquisition side is held open.

At the time of imaging after resetting, the signal component that is being outputted from the pixel section $P_{m,n}$ to the wiring Vline(n) when the set_s signal is switched from a high level to a low level and the switch $SW_{11}$ is opened is, from then onward, held by the capacitor $C_1$ as a voltage value out_s(n). At this time of imaging, the switch $SW_{21}$ on a pixel signal acquisition side is held open.

Then, when the hshift(n) signal becomes a high level, the switch $SW_{12}$ is closed, and the voltage value out_s(n) that has been held by the capacitor $C_1$ is outputted to the wiring Hline_s, and moreover, the switch $SW_{22}$ is closed, and the voltage value out_n(n) that has been held by the capacitor $C_2$ is outputted to the wiring Hline_n. A difference between these voltage values out_s(n) and out_n(n) indicates pixel data according to the amount of electric charge generated by the photodiode PD of the pixel section $P_{m,n}$.

Figure 3:
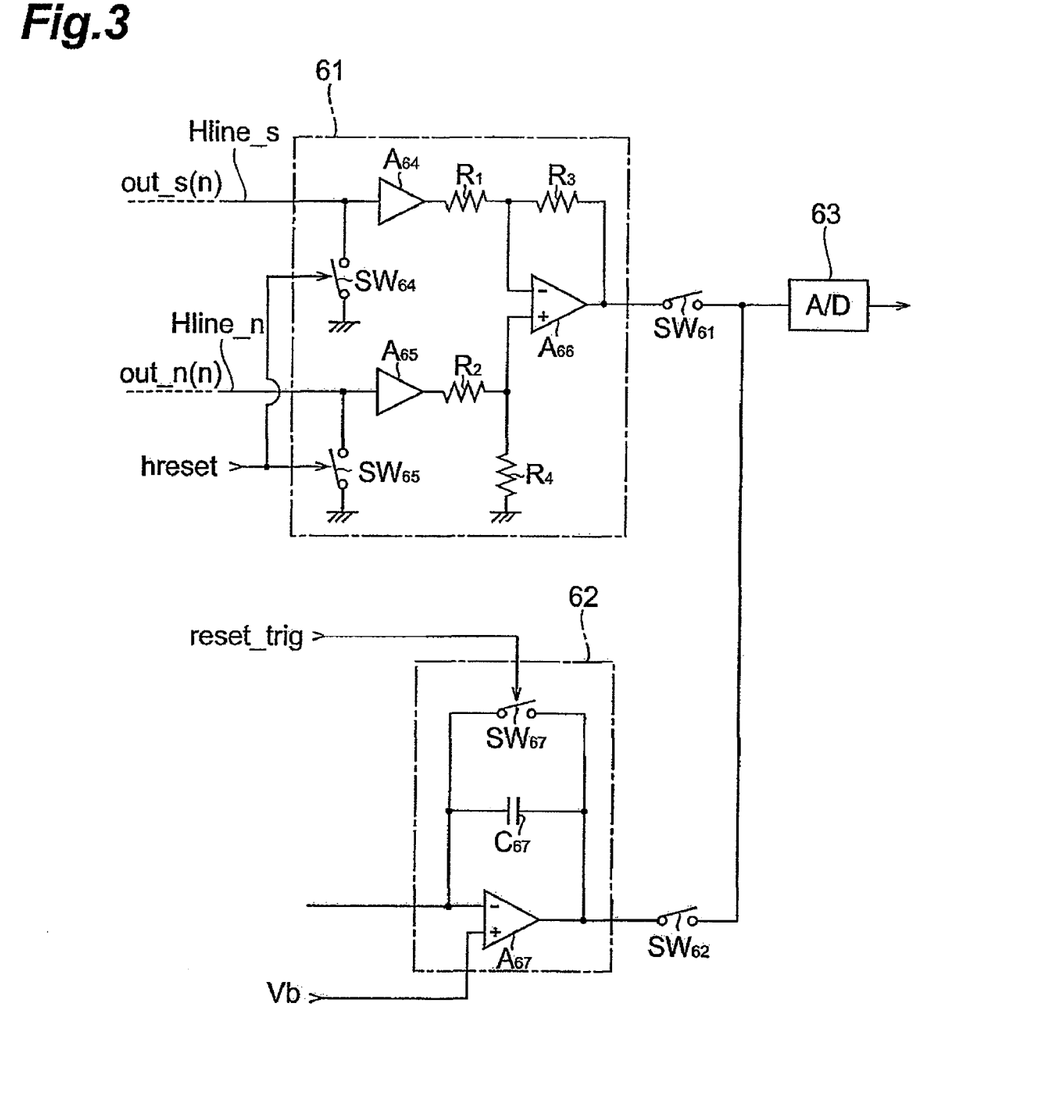
FIG. 3 is a diagram showing circuit configurations of a difference operating circuit 61 and an integrating circuit 62 included in the solid-state image pickup device 1 according to the present embodiment, respectively.

FIG. 3 is a diagram showing circuit configurations of the difference operating circuit 61 and the integrating circuit 62 included in the solid-state image pickup device 1 according to the present embodiment, respectively.

The difference operating circuit 61 includes amplifiers $A_{64}$ to $A_{66}$, switches $SW_{64}$ and $SW_{65}$, and resistors $R_1$ to $R_4$. An inverting input terminal of the amplifier $A_{66}$ is connected with an output terminal of the buffer amplifier $A_{64}$ via the resistor $R_1$, and is connected with an output terminal of itself via the resistor $R_3$. A non-inverting input terminal of the amplifier $A_{66}$ is connected with an output terminal of the buffer amplifier $A_{65}$ via the resistor $R_2$, and is connected with a ground potential via the resistor $R_4$.

The output terminal of the amplifier $A_{66}$ is connected with the switch $SW_{61}$. An input terminal of the buffer amplifier $A_{64}$ is connected with the N holding circuits $H_1$ to $H_N$ via the wiring Hline_s, and is connected with a ground potential via the switch $SW_{64}$. An input terminal of the buffer amplifier $A_{65}$ is connected with the N holding circuits $H_1$ to $H_N$ via the wiring Hline_n, and is connected with a ground potential via the switch $SW_{65}$.

The switches $SW_{64}$ and $SW_{65}$ of the difference operating circuit 61 are controlled by an hreset signal to perform opening/closing operations. As a result of the switch $SW_{64}$ being closed, the voltage value to be inputted to the input terminal of the buffer amplifier $A_{64}$ is initialized. As a result of the switch $SW_{65}$ being closed, the voltage value to be inputted to the input terminal of the buffer amplifier $A_{65}$ is initialized. When the switches $SW_{64}$ and $SW_{65}$ are open, the voltage values out_s(n) and out_n(n) outputted to the wirings Hline_s and Hline_n from any holding circuit $H_n$ of the N holding circuits $H_1$ to $H_N$ are inputted to the input terminals of the buffer amplifiers $A_{64}$ and $A_{65}$. Assuming that each of the buffer amplifiers $A_{64}$ and $A_{65}$ has an amplification factor of 1 and each of the four resistors $R_1$ to $R_4$ has the same resistance value as each other, the voltage value to be outputted from an output terminal of the difference operating circuit 61 indicates a difference between the voltage values to be inputted through the wiring Hline_s and the wiring line_n, respectively.

The integrating circuit 62 includes an amplifier $A_{67}$, a capacitor $C_{67}$, and a switch $SW_{67}$. The capacitor $C_{67}$ and the switch $SW_{67}$ are provided between a non-inverting input terminal and an output terminal of the amplifier $A_{67}$ while being connected in parallel to each other. The non-inverting input terminal of the amplifier $A_{67}$ is connected with the triggering photodetecting section 20. An inverting input terminal of the amplifier $A_{67}$ is connected with a reference potential Vb. The output terminal of the amplifier $A_{67}$ is connected with the switch $SW_{62}$. The switch $SW_{67}$ of the integrating circuit 62 is controlled by a reset_trig signal to perform an opening/closing operation. As a result of the switch $SW_{67}$ being closed, the capacitor $C_{67}$ is discharged, and the voltage value to be outputted from the integrating circuit 62 is initialized. When the switch $SW_{67}$ is open, an electric charge outputted from the triggering photodetecting section 20 is accumulated in the capacitor $C_{67}$, and a voltage value according to the amount of accumulated electric charge is outputted from the integrating circuit 62.

Figure 4:
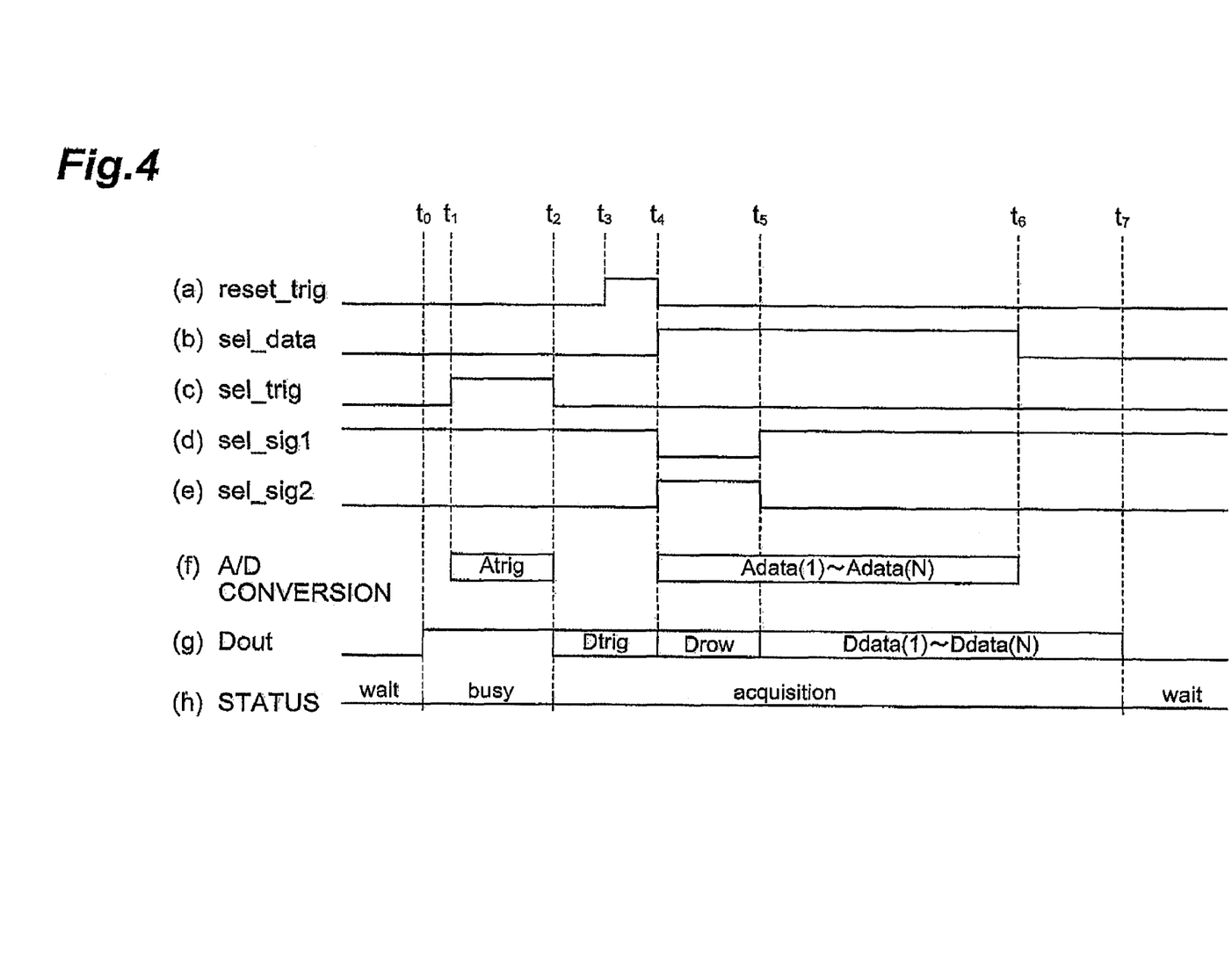
FIG. 4 is a timing chart showing an example of operation of the solid-state image pickup device 1 according to the present embodiment.

Next, description will be given of an example of operation of the solid-state image pickup device 1 according to the present embodiment. FIG. 4 is a timing chart showing an example of operation of the solid-state image pickup device 1 according to the present embodiment, and this corresponds to a period to acquire one time of triggering data and N pieces of pixel data for one row. The solid-state image pickup device 1 operates under the control of the controlling section 70. In this figure, shown in order from the top is, (a) a reset_trig signal that controls an opening/closing operation of the switch $SW_{67}$ of the integrating circuit 62, (b) a sel_data signal that controls an opening/closing operation of the switch $SW_{61}$ of the output section 60, (c) a sel_trig signal that controls an opening/closing operation of the switch $SW_{62}$ of the output section 60, (d) a sel_sig1 signal that controls an opening/closing operation of the switch $SW_{63}$ of the output section 60, (e) a sel_sig2 signal that controls an opening/closing operation of the switch $SW_{68}$ of the output section 60, (f) a voltage value to be a target of an A/D conversion in an A/D converter circuit 63, (g) data Dout to be outputted to the output signal line Lout from the output section 60, and (h) a status of the solid-state image pickup device 1.

Moreover, in this figure, pixel data (analog data) outputted from the holding circuit $H_n$ and to be A/D-converted by the A/D converter circuit 63 is expressed as Adata(n), and triggering data (analog data) outputted from the triggering photodetecting section 20 and to be A/D-converted by the A/D converter circuit 63 is expressed as Atrig. Pixel data (digital data) outputted as a result of the pixel data (analog data) Adata(n) being A/D-converted by the A/D converter circuit 63 is expressed as Ddata(n), and triggering data (digital data) outputted as a result of the triggering data (analog data) Atrig being A/D-converted by the A/D converter circuit 63 is expressed as Dtrig, and row identifying data outputted from the row selecting section 30 is expressed as Drow.

Before time $t_0$, the solid-state image pickup device 1 is in an initial state or in a state after an elapse of a set period of time where the output data Dout was continuously at a low level, and the status is "wait." Thereafter, for a set period from time $t_0$ to time $t_2$, the status of the solid-state image pickup device 1 is "busy," where the output data Dout from the A/D converter circuit 63 is continuously at a high level. For a period from time $t_2$ to time $t_7$, the status of the solid-state image pickup device 1 is "acquisition," where significant data is outputted as the output data Dout. After time $t_7$, the status of the solid-state image pickup device 1 is again "wait," where the output data Dout from the A/D converter circuit 63 is continuously at a low level.

The solid-state image pickup device 1 repeats such operation as in the above, and outputs, in each one period of time where the status is "acquisition," with respect to each row in the imaging photodetecting section 10 sequentially, pixel data of a value according to the amount of electric charge generated by the photodiode of each of the N pixel sections $P_{m,1}$ to $P_{m,N}$. More specifically, in a certain period of time where the status is "acquisition," outputted is pixel data of a value according to the amount of electric charge generated by the photodiode of each of the N pixel sections $P_{m,1}$ to $P_{m,N}$ of a certain m-th row in the imaging photodetecting section 10. In a next period of time where the status is "acquisition," outputted is pixel data of a value according to the amount of electric charge generated by the photodiode of each of the N pixel sections $P_{m+1,1}$ to $P_{m+1,N}$ of the (m+1)-th row in the imaging photodetecting section 10. Moreover, subsequent to the M-th row, outputted is pixel data of a value according to the amount of electric charge generated by the photodiode of each of the N pixel sections $P_{1,1}$ to $P_{1,N}$ of the first row.

For a period from time $t_1$ to time $t_2$, the sel_trig signal becomes a high level, the switch $SW_{62}$ of the output section 60 is closed, and the triggering data (analog data) Atrig outputted from the triggering photodetecting section 20 is A/D-converted by the A/D converter circuit 63. For a subsequent period from time $t_2$ to time $t_4$, the sel_sig1 signal becomes a high level, the switch $SW_{63}$ of the output section 60 is closed, and triggering data (digital data) Dtrig outputted as a result of the triggering data (analog data) Atrig being A/D-converted by the A/D converter circuit 63 is outputted to the output signal line Lout as the output data Dout. For a period from time $t_3$ to time $t_4$, the reset_trig signal becomes a high level, the switch $SW_{67}$ of the integrating circuit 62 is closed, the capacitor $C_{67}$ of the integrating circuit 62 is discharged, and the output voltage of the integrating circuit 62 is initialized.

For a period from time $t_4$ to time $t_5$, the sel_sig2 signal becomes a high level, the switch $SW_{68}$ of the output section 60 is closed, and the row identifying data Drow to be outputted from the row selecting section 30 is outputted to the output signal line Lout as the output data Dout.

For a period from time $t_4$ to time $t_6$, the sel_data signal becomes a high level, the switch $SW_{61}$ of the output section 60 is closed, and pixel data (analog data) Adata(1) to Adata(N) outputted sequentially from the holding circuits $H_1$ to $H_n$ are A/D-converted by the A/D converter circuit 63. Then, for a period from time $t_5$ to time $t_7$, the sel_sig1 signal becomes a high level, the switch $SW_{63}$ of the output section 60 is closed, and pixel data (digital data) Ddata(1) to Ddata(N) outputted as a result of the pixel data (analog data) Adata(1) to Adata(N) being A/D-converted by the A/D converter circuit 63 are sequentially outputted to the output signal line Lout as the output data Dout.

Thus, in the "acquisition" period (time $t_2$ to time $t_7$), the triggering data Dtrig, the row identifying data Drow, and the pixel data Ddata(1) to Ddata(N) in the m-th row indicated by the row identifying data Drow are serially outputted from the output section 60 of the solid-state image pickup device 1 to the common output signal line Lout. As in the above, in the solid-state image pickup device 1 according to the present embodiment, these digital data Dtrig, Drow, and Ddata(1) to Ddata(N) are outputted to the common output signal line Lout by time sharing. Therefore, this solid-state image pickup device 1 suffices with a small number of wirings to input and output signals and the like with an external apparatus and thus has a high reliability as one used in the oral cavity.

Moreover, before the acquisition period (time $t_2$ to time $t_7$), there is a "busy" period (time $t_0$ to time $t_2$) to inform that the "acquisition" period will start, and after the "acquisition" period (time $t_2$ to time $t_7$), there is a wait period (after time $t_7$) to inform that the "acquisition" period has ended. Therefore, the external apparatus used in connection with the solid-state image pickup device 1 can reliably acquire the digital data Dtrig, Drow, and Ddata(1) to Ddata(N) by recognizing information on the status outputted to the signal line Lout. Also, each of the "busy" status and the "wait" status can be recognized by the fact that the output data Dout outputted from the A/D converter circuit 63 is at a high level or a low level for only a set period of time. For example, this set period of time is preferably a period of time for two pieces of data or more.

Moreover, as a result of the "busy" period, the "acquisition" period, and the "wait" period being repeated at a constant frequency, with respect to each row in the imaging photodetecting section 10, pixel data of a value according to the amount of electric charge generated by the photodiode of each of the N pixel sections $P_{m,1}$ to $P_{m,N}$ is outputted sequentially, so that the charge accumulating time in the photodiode PD of each pixel section $P_{m,n}$ is made constant.

Moreover, since the triggering data Dtrig and the row identifying data Drow are outputted in every "acquisition" period, the external apparatus used in connection with the solid-state image pickup device 1 can identify what row the pixel data Ddata(1) to Ddata(N) to be outputted subsequently are in, and can also identify whether the data are ones of an X-ray image (a fluorescent image emitted from a scintillator when an X-ray image is made incident into the scintillator) taken by capturing the timing of incidence of X-rays.

For example, when an incidence of X-rays starts in the period of readout of the (m−1) row, a value equivalent to the incidence of X-rays is outputted from the triggering data at the time of readout of the m-th row. The external apparatus that is used in connection with the solid-state image pickup device 1 can detect an incidence of X-rays based on a signal of the triggering data at the time of readout of the m-th row and acquire pixel data from the m-th row. Thereafter, by acquiring only an integral number of frames of Ddata(1) to Ddata(N) of the m-th row to Ddata(1) to Ddata(N) of the N-th row and Ddata(1) to Ddata(N) of the first row to Ddata(1) to Ddata(N) of the (m−1) row and processing these pixel data, a clear X-ray image can be obtained.

Since an incidence of X-rays is detected based on the value of the triggering data, there is no need for processing by the external apparatus, even if pixel data in a period where no X-rays are irradiated is outputted from the output signal line Lout. Therefore, it is unnecessary to store pixel data in a period of no irradiation in a frame memory. Moreover, when the triggering data is outputted for every row, it becomes possible to judge whether X-rays are being made incident before the pixel data in each row is outputted. This makes it also unnecessary to store data in the first row to the row where an incidence starts in a frame memory, and a load on the external apparatus can also be reduced.

In addition, scintillators are often coupled on incident sections of the imaging photodiodes and triggering photodiode. The scintillators are generally fixed by adhering onto the incident sections of the photodiodes. Thus, the scintillator converts X-rays to a visible light and the photodiode photo-electrically converts the visible light, whereby an electric charge corresponding to the amount of X-ray irradiation is accumulated in the photodiode.

INDUSTRIAL APPLICABILITY

The present invention relates to a solid-state image pickup device having a photodetecting section for which a plurality of photodiodes that each generate electric charge of an amount according to an incident light intensity are arranged two dimensionally, and particularly relates to a solid-state image pickup device that can be suitably used for oral radiography.

The invention claimed is:
1. A solid-state image pickup device comprising:
when M and N are both provided as integers not less than 2, m is provided as an integer not less than 1 and not more than M, and n is provided as an integer not less than 1 and not more than N,
an imaging photodetecting section including pixel sections $P_{1,1}$ to $P_{M,N}$ each having a photodiode that generates electric charge of an amount according to incident light intensity and arrayed two dimensionally in M rows and N columns;

a triggering photodetecting section including a triggering photodiode that generates electric charge of an amount according to incident light intensity; and an output section that outputs pixel data of a value according to the amount of electric charge generated by the photodiode of any pixel section $P_{m,n}$ of the pixel sections $P_{1,1}$ to $P_{M,N}$ and triggering data of a value according to the amount of electric charge generated by the triggering photodiode to a common output signal line, wherein the triggering photodetecting section includes one triggering photodiode provided surrounding the imaging photodetecting section.

2. A solid-state image pickup device comprising:

when M and N are both provided as integers not less than 2, m is provided as an integer not less than 1 and not more than M, and n is provided as an integer not less than 1 and not more than N, an imaging photodetecting section including pixel sections $P_{1,1}$ to $P_{M,N}$ each having a photodiode that generates electric charge of an amount according to incident light intensity and arrayed two dimensionally in M rows and N columns;

a triggering photodetecting section including a triggering photodiode that generates electric charge of an amount according to incident light intensity; and an output section that outputs pixel data of a value according to the amount of electric charge generated by the photodiode of any pixel section $P_{m,n}$ of the pixel sections $P_{1,1}$ to $P_{M,N}$ and triggering data of a value according to the amount of electric charge generated by the triggering photodiode to a common output signal line, wherein the triggering photodetecting section includes a plurality of triggering photodiodes provided around the imaging photodetecting section and connected to each other.

* * * * *